(12) United States Patent
Wang et al.

(10) Patent No.: US 8,753,688 B2
(45) Date of Patent: Jun. 17, 2014

(54) BEAR BILE MACROMOLECULAR EXTRACT AND PREPARATION METHOD AND USE THEREOF

(75) Inventors: Xijun Wang, Harbin (CN); Xiuhong Wu, Harbin (CN); Hui Sun, Harbin (CN); Wenjun Sun, Harbin (CN)

(73) Assignee: Heilongjiang GAP (Good Agriculture Practice) Research Center, Harbin (CN)

( * ) Notice: Subject to any disclaimer, the term of this patent is extended or adjusted under 35 U.S.C. 154(b) by 0 days.

(21) Appl. No.: 13/260,171

(22) PCT Filed: Dec. 10, 2009

(86) PCT No.: PCT/CN2009/001415
§ 371 (c)(1),
(2), (4) Date: Sep. 23, 2011

(87) PCT Pub. No.: WO2010/121404
PCT Pub. Date: Oct. 28, 2010

(65) Prior Publication Data
US 2012/0020895 A1  Jan. 26, 2012

(30) Foreign Application Priority Data
Apr. 24, 2009  (CN) .......................... 2009 1 0082557

(51) Int. Cl.
*A61K 9/00* (2006.01)
*A61P 31/14* (2006.01)

(52) U.S. Cl.
USPC .......................................... 424/528; 424/400

(58) Field of Classification Search
USPC ................................................. 424/528, 400
See application file for complete search history.

(56) References Cited

FOREIGN PATENT DOCUMENTS

| CN | 1057909 C | 11/2000 |
|---|---|---|
| CN | 1212150 C | 7/2005 |
| CN | 101062057 A | 10/2007 |

OTHER PUBLICATIONS

Piao, Huishan, et al., "Study of Quality Standard for Injectable Xiongdan (Bear bile) Powder", Liaoning Journal of Traditional Chinese medicine, vol. 32, No. 11, pp. 1189-1190, 2005.
Lu, Xueqing, at al., "Determination of Phospholipids in Bear Bile by Isocratic High Performance Liquid Chromatography", Chinese Journal of Chromatography, vol. 17, No. 6, pp, 559-562, 1999.

*Primary Examiner* — Rachael E Bredefeld
(74) *Attorney, Agent, or Firm* — Birch, Stewart, Kolasch & Birch, LLP

(57) ABSTRACT

A bear bile macromolecular extract with anti-HCV virus function is disclosed. A preparation method comprises the following steps of: taking fresh bear bile or dissolving bear bile powder with water, centrifuging it by a molecular sieve filter membrane with molecular weight cut-off of 100,000 or an ultrafiltration membrane, filtering to obtain sediment, dissolving the sediment with water, adding the solution to sephadex column, separating the solution by using water or buffer as elution solvent, and freeze-drying the eluent to obtain the bear bile macromolecular extract. Experiments show that the bear bile macromolecular extract has anti-HCV virus function and can be used for treating hepatitis C.

12 Claims, 1 Drawing Sheet

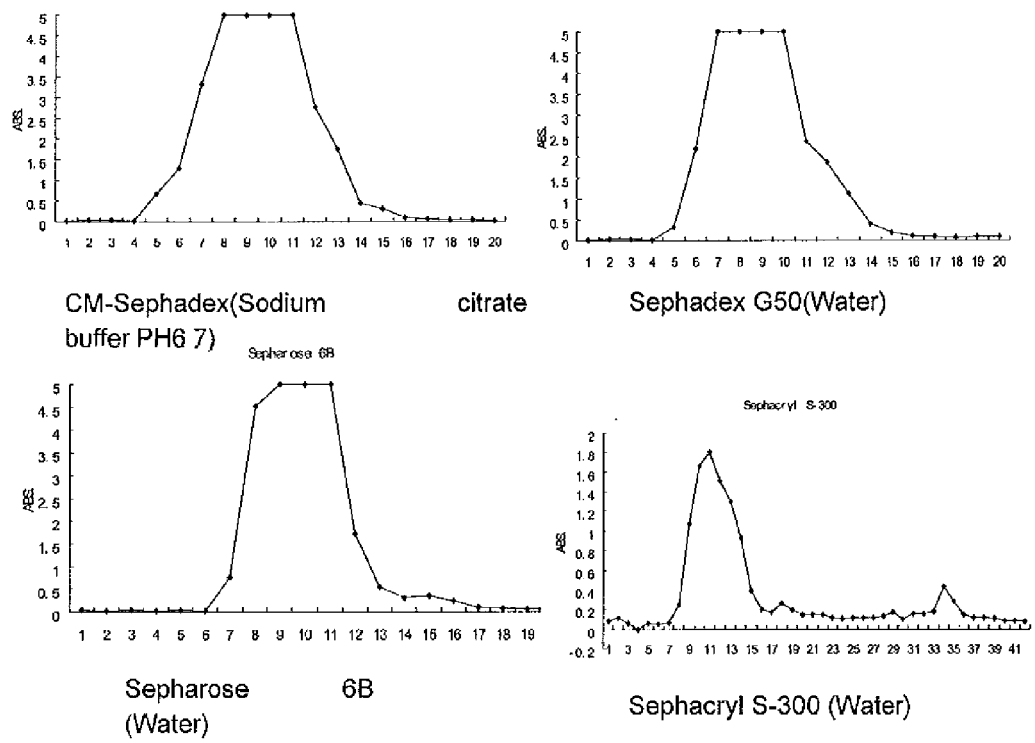

BEAR BILE MACROMOLECULAR EXTRACT AND PREPARATION METHOD AND USE THEREOF

This application is the national stage of International Application No. PCT/CN2009/001415 filed on Dec. 10, 2009, which claims priority under 35 USC §119 of Application No. 200910082557.3 filed in China on Apr. 24, 2009, the entire contents of each of which are hereby incorporated by reference.

TECHNOLOGICAL FIELD

The present invention refers to a bear bile macromolecular extract and preparation method and use thereof. In particular, the present invention refers to a bear bile macromolecular extract with anti-hepatitis C virus function and preparation method and use thereof.

TECHNOLOGICAL BACKGROUND

Hepatitis is an infectious disease caused by hepatitis virus which has wide epidemic range and high incidence. Viral hepatitis is a general designation of hepatitis. Hepatitis C was initially described as non A and non B-post transfusion hepatitis. In 1989, hepatitis C virus cDNA was cloned successfully from the blood of an infected chimpanzee by Choo et al., which confirms hepatitis C virus is the pathogen of hepatitis C. Hepatitis C is a virus infectious and worldwide spread disease. It can cause a wide, formidable and chronic infection and make more people die compared with AIDS. The amount of HCV infected patients is been 3 times of that of AIDS infected patients. 2%~3% in global population, 0.7%~3.1% in Chinese population. 80% of HCV infectors may develop into chronic hepatitis, at least 20% will progress to cirrhosis, and 15% may develop metastasis of liver cancer. It is estimated 1.7 billion people are infected by virus which can cause permanent liver injury, even death.

There is no specific for HCV at present. Nucleoside analogues, ribavirin (and nucleotide trinitro), acyclovir (acycloguanosine), ganciclovir and so on, are used clinically. As an old product of nucleoside analogues, ribavirin has strong effect on blocking the replication of hepatitis C virus. Especially, hepatitis C is combined treated by interferon and ribavirin, by which the disease is controlled. But the virus cannot be cleaned. Sustained virologic response rate of it is not satisfied. Only 50% patients respond to it completely. For patients with HCV/HIV co-infection, the percentage decrease to 30%. In addition, nucleoside analogues cost too much and make patients bounce back to bad health if they stop taking them and result in a series of harm because of their side effect. So the urgent matter is to find anti-HCV drug with high efficiency and low toxicity.

In recent years, with further study on replication steps in lifecycle of HCV virus, some promising drug targets are found, such as HCV NS3 protease. In the replication process of HCV, it is a necessary protease. The encode of this protease is serine protease and nucleoside triphosphatase/helicase. The protease needs NS4A protein to be cofactor to make activity optimize. HCV NS3/4A protease is a key enzyme in viral replication and formation of infection virus particles and a charming target of HCV inhibitor. It is effective way to search and discover HCV N3/4A protease inhibitor to discover anti-HCV drugs.

CONTENT OF THE INVENTION

One aspect of the present invention is to provide a bear bile macromolecular extract with anti-hepatitis C virus function (HCV NS3/4A protease inhibition); another aspect of this invention is to provide a method of preparing the macromolecular extract; the aspect of this invention is also to provide use of the extract.

The present invention can be implemented through the following technics:

The preparation method of bear bile macromolecular extract of the present invention includes the following steps:

Add water to dissolve bear bile powder to obtain aqueous solution of bear bile in concentration of 10~100 mg/ml, centrifuge the solution by a molecular sieve filter membrane with molecular weight cut-off of 100,000 at the centrifugal force of 4000×g for 10-60 minutes, or centrifuge fresh bear bile by a molecular sieve filter membrane with molecular weight cut-off of 100,000 at the centrifugal force of 4000×g for 1-2 hours; filter to obtain a sediment, dissolve the sediment in water, add the solution to a pretreated cross-linked dextran SEPHADEX®-G100 column, separate the solution by using water or buffer as the elution solvent, collect the eluent with absorption at 280 nm, freeze-dry to obtain the bear bile macromolecular extract.

The preparation method of bear bile macromolecular extract of the present invention can be optimized as the following steps:

Add water to dissolve bear bile powder to obtain aqueous solution of bear bile in concentration of 50 mg/ml, centrifuge the solution by a molecular sieve filter membrane with molecular weight cut-off of 100,000 at the centrifugal force of 4000×g for 30 minutes, or centrifuge fresh bear bile by a molecular sieve filter membrane with molecular weight cut-off of 100,000 at the centrifugal force of 4000×g for 1.5 hours; filter to obtain a sediment, dissolve the sediment in water, add the solution to a pretreated cross-linked dextran SEPHADEX®-G100 column, separate the solution by using water or buffer as the elution solvent, collect the eluent with absorption at 280 nm, freeze-dry to obtain the bear bile macromolecular extract.

The preparation method of bear bile macromolecular extract of the present invention can be optimized the following steps:

Add water to dissolve bear bile powder to obtain aqueous solution of bear bile in concentration of 20 mg/ml, centrifuge the solution by a molecular sieve filter membrane with molecular weight cut-off of 100,000 at the centrifugal force of 4000×g for 15 minutes; or centrifuge fresh bear bile by a molecular sieve filter membrane with molecular weight cut-off of 100,000 at the centrifugal force of 4000×g for 1 hour; filter to obtain a sediment, dissolve the sediment in water, add the solution to a pretreated cross-linked dextran SEPHADEX®-G100 column, separate the solution by using water or buffer as the elution solvent, collect the eluent with absorption at 280 nm, freeze-dry to obtain the bear bile macromolecular extract.

The preparation method of bear bile macromolecular extract of the present invention can be optimized the following steps:

Add water to dissolve bear bile powder to obtain aqueous solution of bear bile in concentration of 90 mg/ml, centrifuge the solution by a molecular sieve filter membrane with molecular weight cut-off of 100,000 at the centrifugal force of 4000×g for 50 minutes; or centrifuge fresh bear bile by a molecular sieve filter membrane with molecular weight cut-off of 100,000 at the centrifugal force of 4000×g for 2 hours;

filter to obtain a sediment, dissolve the sediment in water, add the solution to a pretreated cross-linked dextran SEPHADEX®-G100 column, separate the solution by using water or buffer as the elution solvent, collect the eluent with absorption at 280 nm, freeze-dry to obtain the bear bile macromolecular extract.

Wherein said buffer is phosphate buffer, citrate buffer or acetate buffer; said molecular sieve filter membrane with molecular weight cut-off of 100,000 can be replaced by ultrafiltration membrane with molecular weight cut-off of 100,000; said cross-linked dextran SEPHADEX®-G100 column having a globular protein fractionation range of 4,000-50,000 can be replaced by other cross-linked dextran columns such as cross-linked dextran SEPHADEX®-G150 having a globular protein fractionation range of 5,000-300,000, crosslinked dextran SEPHADEX®-G200 having a globular protein fractionation average of 5,000-600,000, or allyl dextran and N,N'-methylene bisacrylamide SEPHACRYL®S-100 or cross-linked dextran SEPHADEX®DEAE-A50.

Add conventional excipient to bear bile macromolecular extract of the present invention, according to conventional technics, to obtain clinical or pharmaceutical acceptable dosage forms, powder injection, injection, aerosols, suppository, lotion, patch, unguentum and so on, dosage forms administrated by muscle, vein, subcutaneous or mucosa; capsule, tablet, sustained-release agent and oral liquid.

The present invention provides new method to treat hepatitis C by bear bile macromolecular extract and compound preparation containing bear bile macromolecular extract. Bear bile powder has the effectiveness of resisting HCV NS3/4A protease, which will be a new highlight in searching and developing anti-HCV drugs. The characteristic of little side effect of Chinese medicine will also make bear bile powder to be safer drug with high titer and avoid iatrogenic disease. The success research and produce of it will make about 2%~3% HCV infector worldwide end the scourge that HCV develops into chronic hepatitis, cirrhosis or liver cancer and have good health, at the same time, remove HCV from the disease spectrum affecting human health severely.

BRIEF DESCRIPTION OF THE DRAWING

FIG. 1 shows comparison of separation effect of active fraction by using different cross-linked dextrans monitored on 280 nm.

The following experiments are further described but not limited to the present invention.

Experiment 1

Comparison of Anti-HCV Virus PR Effect Between Bear Bile Powder and Biles of Other Animals 1. Reagent Used in Activity Assay:
Substrate: HCV NS3/4A protease substrate
Protease: HCV NS3/4A protease
Detector: fluoresce detector (Ex/Em=485/535 nm)
2. Activity Assay Results
Compare the inhibition effect of biles of different animals on HCV PR by activity assay method of HCV PR activity. The result shows the $IC_{50}$ of bear bile is 0.2 ug/ml. The high activity is rarely reported whatever in Chinese Traditional Medicine or Western Medicine, however, bile of other animals have no such effect or weak effect (Table 1).

TABLE 1

Comparison of anti-HCV virus effect of bear bile and bile of other animals

| Sample | 100 μg/ml | 10 μg/ml | 1 μg/ml | 0.1 μg/ml | Median effect concentration $IC_{50}$ (μg/ml) |
| --- | --- | --- | --- | --- | --- |
| Bear bile | 91.9 ± 1.6 | 78.9 ± 5.3 | 64.8 ± 6.5 | 44.0 ± 0.4 | 0.2 |
| Chick bile | 5.1 ± 4.5 | — | — | — | >100 |
| Duck bile | 5.8 ± 3.3 | — | — | — | >100 |
| Pig bile | 68.7 ± 5.0 | 10.9 ± 5.1 | — | — | 48.4 |
| Sheep bile | 1.7 ± 1.5 | — | — | — | >100 |
| Ox bile | 34.1 ± 3.3 | — | — | — | >100 |

Experiment 2

The Activity Research on Anti-HCV PR of Bear Bile Macromolecular Extract of the Present Invention 1. Centrifugal Separation
Material: Millipore molecular sieve filter membrane (molecular weight cut-off: 100,000)
Sample solution: aqueous solution of bear bile powder part with different molecular weight in concentration 25 mg/ml
Centrifugation conditions: centrifuge at the centrifugal force of 4000×g for 20 minutes.

Freeze-dry solution of the two part are obtained by centrifugal separation or membrane filtration separation respectively, and are assayed the activity according to the same method described in Experiment 1, see Table 2;

TABLE 2

Comparison result of anti-HCV PR activity of different fractions obtained by centrifugal separation

| Fraction | Inhibition rate ± S.D/% |
| --- | --- |
| molecular weight > 100k | 91.20 ± 1.41 |
| molecular weight < 100k | 24.32 ± 3.99 |

The assay result shows, anti-HCV PR active part of bear bile powder is macromolecular substances with molecular weight greater than 100,000.
2. Further Separation of Active Fraction
(1) Separated by Cross-Linked Dextran SEPHADEX®-G100
Pretreat cross-linked dextran SEPHADEX®-G100 according to the requirement, pack the column; add water to dissolve bear bile powder to obtain aqueous solution of bear bile in concentration of 20 mg/ml, centrifuge the solution by a molecular sieve filter membrane with molecular weight cut-off of 100,000 at the centrifugal force of 4000×g for 15 minutes, or centrifuge fresh bear bile by a molecular sieve filter membrane with molecular weight cut-off of 100,000 at the centrifugal force of 4000×g for 1 hour; filter to obtain a sediment, dissolve the sediment in water, add the solution to the column, use water as elution solvent, obtain four eluted fractions: 1. yellow, having strong absorption at 280 nm: 2. light yellow, having weak absorption at 280 nm; 3. almost colorless, having no absorption at 280 nm; 4. colorless, having no absorption at 280 nm. Active part is mainly the first fraction having strong absorption at 280 nm. Assay the activity according to the same method described in Experiment 1, see Table 3;

TABLE 3

Anti-HCV PR assay results of different eluted fractions (100 μg/ml)

| Fraction | Inhibition rate ± S.D/% |
|---|---|
| 1 | 95.7 ± 4.7 |
| 2 | 12.6 ± 2.4% |
| 3 | 5.3 ± 3.9% |
| 4 | −3.5 ± 14.1% |

(2) Separating Effect of Other Types of Fillers

Use CM-cross-linked dextran SEPHADEX®, cross-linked dextran SEPHADEX® G50, Sepharose 6B and allyl dextran and N,N'-methylene bisacrylamide SEPHACRYL® S-300 as separating column filler respectively, add water to dissolve bear bile powder to obtain aqueous solution of bear bile in concentration of 20 mg/ml, centrifuge the solution by a molecular sieve filter membrane with molecular weight cut-off of 100,000 at the centrifugal force of 4000×g for 15 minutes; or centrifuge fresh bear bile by a molecular sieve filter membrane with molecular weight cut-off of 100,000 at the centrifugal force of 4000×g for 1 hour; filter to obtain a sediment, dissolve the sediment in water, add the solution to the column, use water or buffer as elution solvent, collect the eluent at the speed of 3 ml/component, monitor separating effect at 280 nm. The result shows that four types of fillers cannot achieve the aim of further separation.

The following examples have the same effect as above experiments.

DETAILED DESCRIPTION OF THE INVENTION

Example 1

Preparation of Injection

Add water to dissolve bear bile powder to obtain aqueous solution of bear bile in concentration of 50 mg/ml, centrifuge the solution by a molecular sieve filter membrane with molecular weight cut-off of 100,000 at the centrifugal force of 4000×g for 30 minutes, filter to obtain a sediment, dissolve the sediment in water, add the solution to a pretreated cross-linked dextran SEPHADEX®-G100 column, separate the solution by water as elution solvent, collect the eluent with absorption at 280 nm, freeze-dry to get the bear bile macromolecular extract, add conventional excipients, obtain injection according to conventional technics.

Example 2

Preparation of Powder Injection

Add water to dissolve bear bile powder to obtain aqueous solution of bear bile in concentration of 20 mg/ml, centrifuge the solution by a molecular sieve filter membrane with molecular weight cut-off of 100,000 at the centrifugal force of 4000×g for 15 minutes, filter to obtain a sediment, dissolve the sediment in water, add the solution to a pretreated cross-linked dextran SEPHADEX®-G100 column, separate the solution by phosphate buffer as elution solvent, collect the eluent with absorption at 280 nm, freeze-dry to get the bear bile macromolecular extract, add conventional excipients, obtain powder injection according to conventional technics.

Example 3

Preparation of Erosols

Add water to dissolve bear bile powder to obtain aqueous solution of bear bile in concentration of 90 mg/ml, centrifuge the solution by a molecular sieve filter membrane with molecular weight cut-off of 100,000 at the centrifugal force of 4000×g for 50 minutes, filter to obtain a sediment, dissolve the sediment in water, add the solution to a pretreated cross-linked dextran SEPHADEX®-G100 column, separate the solution by citrate buffer as elution solvent, collect the eluent with absorption at 280 nm, freeze-dry to get the bear bile macromolecular extract, add conventional excipients, obtain erosols according to conventional technics.

Example 4

Preparation of Suppository

Centrifuge fresh bear bile by a molecular sieve filter membrane with molecular weight cut-off of 100,000 at the centrifugal force of 4000×g for 1 hour; filter to obtain a sediment, dissolve the sediment in water, add the solution to a pretreated cross-linked dextran SEPHADEX®-G100 column, separate the solution by water as elution solvent, collect the eluent with absorption at 280 nm, freeze-dry to obtain the bear bile macromolecular extract, add conventional excipients, obtain suppository according to conventional technics.

Example 5

Preparation of Lotion

Centrifuge fresh bear bile by a molecular sieve filter membrane with molecular weight cut-off of 100,000 at the centrifugal force of 4000×g for 2 hours; filter to obtain a sediment, dissolve the sediment in water, add the solution to a pretreated cross-linked dextran SEPHADEX®-G100 column, separate the solution by water as elution solvent, collect the eluent with absorption at 280 nm, freeze-dry to obtain the bear bile macromolecular extract, add conventional excipients, obtain lotion according to conventional technics.

Example 6

Preparation of Unguentum

Centrifuge fresh bear bile by a molecular sieve filter membrane with molecular weight cut-off of 100,000 at the centrifugal force of 4000×g for 1.5 hours; filter to obtain a sediment, dissolve the sediment in water, add the solution to a pretreated allyl dextran and N,N'-methylene bisacrylamide SEPHACRYL® column S-100, separate the solution by water as elution solvent, collect the eluent with absorption at 280 nm, freeze-dry to obtain the bear bile macromolecular extract, add conventional excipients, obtain unguentum according to conventional technics.

Example 7

Preparation of Capsule

Add water to dissolve bear bile powder to obtain aqueous solution of bear bile in concentration of 50 mg/ml, centrifuge the solution by a molecular sieve filter membrane with molecular weight cut-off of 100,000 at the centrifugal force of 4000×g for 30 minutes, filter to obtain a sediment, dissolve the sediment in water, add the solution to a pretreated cross-linked dextran SEPHADEX® column DEAE-A50, separate the solution by acetate buffer as elution solvent, collect the eluent with absorption at 280 nm, freeze-dry to get the bear bile macromolecular extract, add conventional excipients, obtain capsule according to conventional technics.

Example 8

Preparation of Oral Liquid

Add water to dissolve bear bile powder to obtain aqueous solution of bear bile in concentration of 20 mg/ml, centrifuge the solution by a molecular sieve filter membrane with molecular weight cut-off of 100,000 at the centrifugal force of 4000×g for 15 minutes, filter to obtain a sediment, dissolve the sediment in water, add the solution to a pretreated cross-linked dextran SEPHADEX®-G100 column, separate the solution by citrate buffer as elution solvent, collect the eluent with absorption at 280 nm, freeze-dry to get the bear bile macromolecular extract, add conventional excipients, obtain oral liquid according to conventional technics.

The invention claimed is:

1. A bear bile macromolecular extract with anti-hepatitis C virus function, characterized in that the extract is prepared by the following method:
add water to dissolve bear bile powder to obtain aqueous solution of bear bile in concentration of 10~100 mg/ml, centrifuge the solution by a molecular sieve filter membrane with molecular weight cut-off of 100,000 at the centrifugal force of 4000×g for 10~60 minutes, or centrifuge fresh bear bile by a molecular sieve filter membrane with molecular weight cut-off of 100,000 at the centrifugal force of 4000×g for 1~2 hours; filter to obtain a sediment, dissolve the sediment in water to obtain a solution, add the solution to a pretreated cross-linked dextran column having a dry particle size of 40 μm-120 μm and a globular protein fractionation range of $4 \times 10^3$-$1.5 \times 10^5$, separate the solution by using water or buffer as elution solvent, collect the eluent, including the void volume eluent, with absorption at 280 nm, freeze-dry the collected eluent to obtain the bear bile macromolecular extract.

2. A bear bile macromolecular extract according to claim 1, characterized in that the extract is prepared by the following method:
add water to dissolve bear bile powder to obtain aqueous solution of bear bile in concentration of 50 mg/ml, centrifuge the solution by a molecular sieve filter membrane with molecular weight cut-off of 100,000 at the centrifugal force of 4000×g for 30 minutes, or centrifuge fresh bear bile by a molecular sieve filter membrane with molecular weight cut-off of 100,000 at the centrifugal force of 4000×g for 1.5 hours; filter to obtain a sediment, dissolve the sediment in water to obtain a solution, add the solution to a pretreated cross-linked dextran column having a dry particle size of 40 μm-120 μm and a globular protein fractionation range of $4 \times 10^3$-$1.5 \times 10^5$, separate the solution by using water or buffer as elution solvent, collect the eluent, including the void volume eluent, with absorption at 280 nm, freeze-dry the collected eluent to obtain the bear bile macromolecular extract.

3. A bear bile macromolecular extract according to claim 1, characterized in that the extract is prepared by the following method:
add water to dissolve bear bile powder to obtain aqueous solution of bear bile in concentration of 20 mg/ml, centrifuge the solution by a molecular sieve filter membrane with molecular weight cut-off of 100,000 at the centrifugal force of 4000×g for 15 minutes, or centrifuge fresh bear bile by a molecular sieve filter membrane with molecular weight cut-off of 100,000 at the centrifugal force of 4000×g for 1 hour; filter to obtain a sediment, dissolve the sediment in water to obtain a solution, add the solution to a pretreated cross-linked dextran column having a dry particle size of 40 μm-120 μm and a globular protein fractionation range of $4 \times 10^3$-$1.5 \times 10^5$, separate the solution by using water or buffer as elution solvent, collect the eluent, including the void volume eluent, with absorption at 280 nm, freeze-dry the collected eluent to obtain the bear bile macromolecular extract.

4. A bear bile macromolecular extract according to claim 1, characterized in that the extract is prepared by the following method:
add water to dissolve bear bile powder to obtain aqueous solution of bear bile in concentration of 90 mg/ml, centrifuge the solution by a molecular sieve filter membrane with molecular weight cut-off of 100,000 at the centrifugal force of 4000×g for 50 minutes, or centrifuge fresh bear bile by a molecular sieve filter membrane with molecular weight cut-off of 100,000 at the centrifugal force of 4000×g for 2 hours; filter to obtain a sediment, dissolve the sediment in water to obtain a solution, add the solution to a pretreated cross-linked dextran column having a dry particle size of 40 μm-120 μm and a globular protein fractionation range of $4 \times 10^3$-$1.5 \times 10^5$, separate the solution by using water or buffer as elution solvent, collect the eluent, including the void volume eluent, with absorption at 280 nm, freeze-dry the collected eluent to obtain the bear bile macromolecular extract.

5. A bear bile macromolecular extract with anti-hepatitis C virus function, characterized in that the extract is prepared by the following method:
add water to dissolve bear bile powder to obtain aqueous solution of bear bile in concentration of 10~100 mg/ml, centrifuge the solution by a molecular sieve filter membrane with molecular weight cut-off of 100,000 at the centrifugal force of 4000×g for 10-60 minutes, or centrifuge fresh bear bile by a molecular sieve filter membrane with molecular weight cut-off of 100,000 at the centrifugal force of 4000×g for 1-2 hours; filter to obtain a sediment, dissolve the sediment in water to obtain a solution, add the solution to a pretreated cross-linked dextran column; separate the solution by using water or buffer as elution solvent, collect the eluent, including the void volume eluent, with absorption at 280 nm, freeze-dry the collected eluent to obtain the bear bile macromolecular extract wherein said buffer is phosphate buffer, citrate buffer or acetate buffer; said molecular sieve filter membrane with molecular weight cut-off of 100,000 is ultrafiltration membrane with molecular weight cut-off of 100,000; and said cross-linked dextran column is selected from the group consisting of a cross-linked dextran having a dry particle size of 40 µm-120 µm and a globular protein fractionation range of $4 \times 10^3 \sim 1.5 \times 10^5$; a cross-linked dextran having a dry particle size of 40 µm~120 µm and a globular protein fractionation range of $5 \times 10^3\text{-}3.0 \times 10^5$; and a cross-linked dextran having a dry particle size of 40 µm-120 µm and a globular protein fractionation range of $5 \times 10^3 \sim 6.0 \times 10^5$, or is allyl dextran and N,N'-methylene bisacrylamide having a dry particle size of 25 µm-75 µm and a globular protein fractionation range of $1.0 \times 10^3\text{-}1.0 \times 10^5$ or is cross-linked dextran DEAE (diethylaminoethyl) having a dry particle size of 40 µm-120 µm and a globular protein fractionation range of $1.5 \times 10^3\text{-}3 \times 10^4$.

6. A bear bile macromolecular extract according to claim 1, characterized in that the bear bile macromolecular extract, according to conventional techniques, is prepared to clinical or pharmaceutical acceptable dosage forms, which are powder injection, injection, aerosol, suppository, lotion, patch, unguentum, capsule, tablet, sustained-release dosage form or oral liquid, by adding conventional excipients.

7. A bear bile macromolecular extract according to claim 5, characterized in that the bear bile macromolecular extract, according to conventional techniques, is prepared to clinical or pharmaceutical acceptable dosage forms, which are powder injection, injection, aerosols, suppository, lotion, patch, unguentum, capsules, tablets, sustained-release dosage form or oral liquid, by adding conventional excipients.

8. A preparation method of a bear bile macromolecular extract with anti-hepatitis C virus function, characterized in that the method includes the following steps:

add water to dissolve bear bile powder to obtain aqueous solution of bear bile in concentration of 10~100 mg/ml, centrifuge the solution by a molecular sieve filter membrane with molecular weight cut-off of 100,000 at the centrifugal force of 4000×g for 10-60 minutes, or centrifuge fresh bear bile by a molecular sieve filter membrane with molecular weight cut-off of 100,000 at the centrifugal force of 4000×g for 1-2 hours; filter to obtain a sediment, dissolve the sediment in water to obtain a solution, add the solution to a pretreated cross-linked dextran column having a dry particle size of 40 µm-120 µm and a globular protein fractionation range of $4 \times 10^3 \sim 1.5 \times 10^5$, separate the solution by using water or buffer as elution solvent, collect the eluent, including the void volume eluent, with absorption at 280 nm, freeze-dry the collected eluent to obtain the bear bile macromolecular extract.

9. A preparation method of a bear bile macromolecular extract according to claim 8, characterized in that the method includes the following steps:

add water to dissolve bear bile powder to obtain aqueous solution of bear bile in concentration of 50 mg/ml, centrifuge the solution by a molecular sieve filter membrane with molecular weight cut-off of 100,000 at the centrifugal force of 4000×g for 30 minutes, or centrifuge fresh bear bile by a molecular sieve filter membrane with molecular weight cut-off of 100,000 at the centrifugal force of 4000×g for 1.5 hours; filter to obtain a sediment, dissolve the sediment in water to obtain a solution, add the solution to a pretreated cross-linked dextran column having a dry particle size of 40 µm~120 µm and a globular protein fractionation range of $4 \times 10^3\text{-}1.5 \times 10^5$, separate the solution by using water or buffer as elution solvent, collect the eluent, including the void volume eluent, with absorption at 280 nm, freeze-dry the collected eluent to obtain the bear bile macromolecular extract.

10. A preparation method of a bear bile macromolecular extract according to claim 8, characterized in that the method includes the following steps:

add water to dissolve bear bile powder to obtain aqueous solution of bear bile in concentration of 20 mg/ml, centrifuge the solution by a molecular sieve filter membrane with molecular weight cut-off of 100,000 at the centrifugal force of 4000×g for 15 minutes, or centrifuge fresh bear bile by a molecular sieve filter membrane with molecular weight cut-off of 100,000 at the centrifugal force of 4000×g for 1 hour; filter to obtain a sediment, dissolve the sediment in water to obtain a solution, add the solution to a pretreated cross-linked dextran column having a dry particle size of 40 µm-120 µm and a globular protein fractionation range of $4 \times 10^3\text{-}1.5 \times 10^5$, separate the solution by using water or buffer as elution solvent, collect the eluent, including the void volume eluent, with absorption at 280 nm, freeze-dry the collected eluent to obtain the bear bile macromolecular extract.

11. A preparation method of a bear bile macromolecular extract according to claim 8, characterized in that the method includes the following steps:

add water to dissolve bear bile powder to obtain aqueous solution of bear bile in concentration of 90 mg/ml, centrifuge the solution by a molecular sieve filter membrane with molecular weight cut-off of 100,000 at the centrifugal force of 4000×g for 50 minutes, or centrifuge fresh bear bile by a molecular sieve filter membrane with molecular weight cut-off of 100,000 at the centrifugal force of 4000×g for 2 hours; filter to obtain a sediment, dissolve the sediment in water to obtain a solution, add the solution to a pretreated cross-linked dextran column having a dry particle size of 40 µm~120 µm and a globular protein fractionation range of $4 \times 10^3\text{-}1.5 \times 10^5$, separate the solution by using water or buffer as elution solvent, collect the eluent, including the void volume eluent, with absorption at 280 nm, freeze-dry the collected eluent to obtain the bear bile macromolecular extract.

12. A preparation method of a bear bile macromolecular extract with anti-hepatitis C virus function, characterized in that the method includes the following steps:

add water to dissolve bear bile powder to obtain aqueous solution of bear bile in concentration of 10-100 mg/ml, centrifuge the solution by a molecular sieve filter membrane with molecular weight cut-off of 100,000 at the centrifugal force of 4000×g for 10~60 minutes, or centrifuge fresh bear bile by a molecular sieve filter membrane with molecular weight cut-off of 100,000 at the centrifugal force of 4000×g for 1-2 hours; filter to obtain a sediment, dissolve the sediment in water to obtain a solution, add the solution to a pretreated cross-linked dextran column; separate the solution by using water or buffer as elution solvent, collect the eluent, including the void volume eluent, with absorption at 280 nm, freeze-dry the collected eluent to obtain the bear bile macromolecular extract wherein said buffer is phosphate buffer, citrate buffer or acetate buffer; said molecular sieve filter membrane with molecular weight cut-off of 100,000 is ultrafiltration membrane with molecular weight cut-off of 100,000; and said cross-linked column is selected from the group consisting of a cross-linked dextran having a dry particle size of 40 μm-120 μm and a globular protein fractionation range of $4 \times 10^3$-$1.5 \times 10^5$; a cross-linked dextran having a dry particle size of 40 μm-120 μm and a fractionation range of $5 \times 10^3$~$3.0 \times 10^5$; and a cross-linked dextran having a dry particle size of 40 μm~120 μm and a globular protein fractionation range of $5 \times 10^3$-$6.0 \times 10^5$, or is allyl dextran and N,N'-methylene bisacrylamide having a dry particle size of 25 μm-75 μm and a globular protein fractionation range of $1.0 \times 10^3$-$1.0 \times 10^5$ or is cross-linked dextran with DEAE having a dry particle size of 40 μm-120 μm and a globular protein fractionation range of $1.5 \times 10^3$-$3 \times 10^4$.

* * * * *